United States Patent [19]
Marotta

[11] Patent Number: 5,314,428
[45] Date of Patent: May 24, 1994

[54] HYDRAULICALLY FLEXING CATHETER

[76] Inventor: Louis C. Marotta, P.O. Box 372, Westport, N.Y. 12993

[21] Appl. No.: 997,314

[22] Filed: Dec. 28, 1992

[51] Int. Cl.$^5$ .............................................. A61M 37/00
[52] U.S. Cl. ........................................ 604/95; 604/97; 128/657
[58] Field of Search ...................... 604/95, 97–101, 604/191, 280–283; 128/657, 658, 772, DIG. 12

[56] References Cited

U.S. PATENT DOCUMENTS

| | | | |
|---|---|---|---|
| 3,467,096 | 9/1969 | Horn | 604/191 |
| 3,773,034 | 11/1973 | Burns et al. | 128/657 X |
| 4,406,656 | 9/1983 | Hattler et al. | 604/280 |
| 4,609,371 | 9/1986 | Pizzino | 604/191 |
| 4,673,395 | 6/1987 | Phillips | 604/191 |
| 4,717,379 | 1/1988 | Ekholmer | 604/280 X |
| 4,796,637 | 1/1989 | Mascuch et al. | 604/280 X |
| 4,983,165 | 1/1991 | Loiterman | 604/95 |
| 5,059,170 | 10/1991 | Cameron | 604/283 X |
| 5,123,421 | 6/1992 | Sinofsky | 604/95 |
| 5,171,216 | 12/1992 | Dasse et al. | 604/283 X |

FOREIGN PATENT DOCUMENTS 0172542 2/1986 European Pat. Off. ............. 604/97

Primary Examiner—C. Fred Rosenbaum
Assistant Examiner—Frank Wilkens
Attorney, Agent, or Firm—Richard L. Miller

[57] ABSTRACT

A catheter has a radially expandable end region containing a plurality of fluid containing channels. A circular assembly containing a plurality of cylinders each containing a piston is arranged so that each piston is connected with one channel. A rotary mechanical assembly is connected so that movement of an arm extending from the rotary assembly causes actuation of one or more pistons to cause selected channels in the catheter to be pressurized, expanding the radial portion of the catheter adjacent the pressurized channels and enabling the catheter to be more easily guided in the desired direction through bodily passageways.

7 Claims, 1 Drawing Sheet

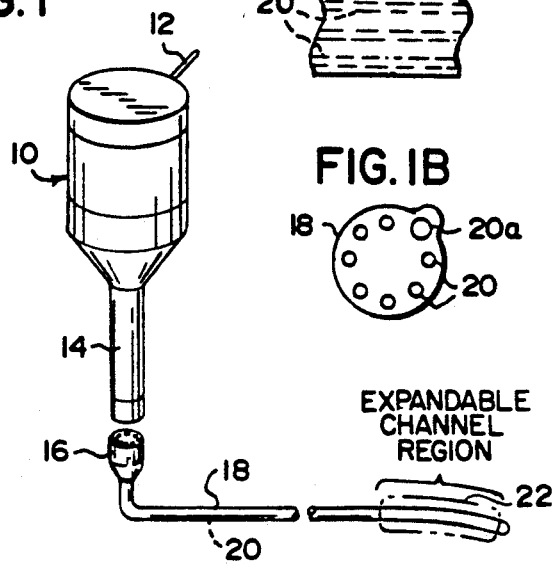
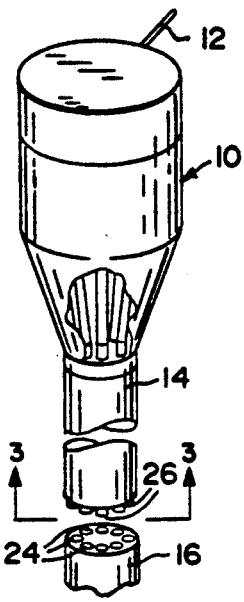
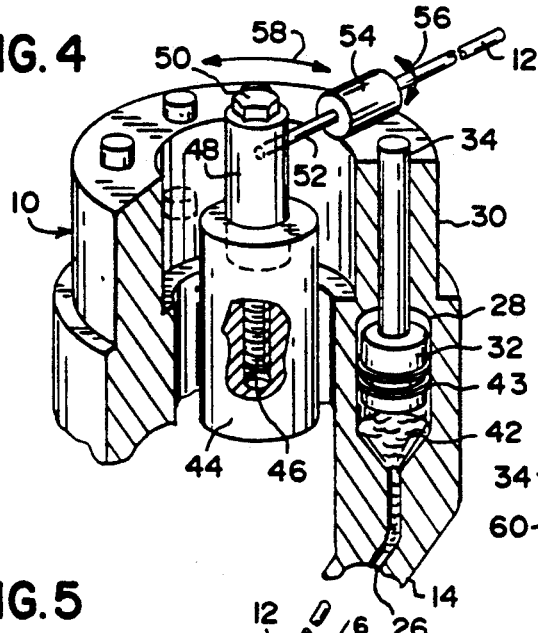
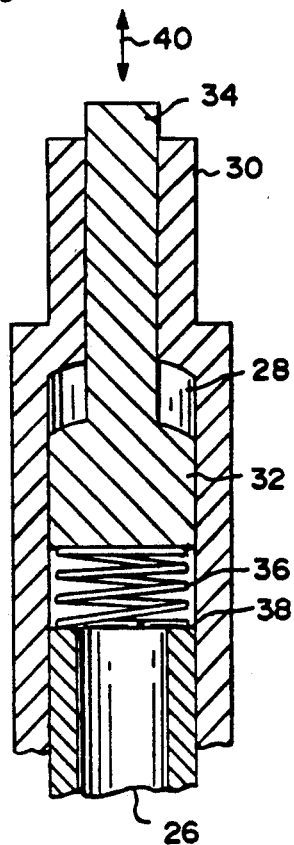
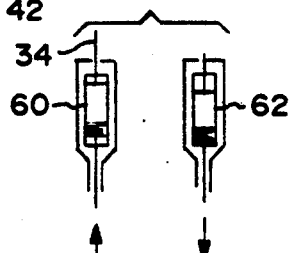
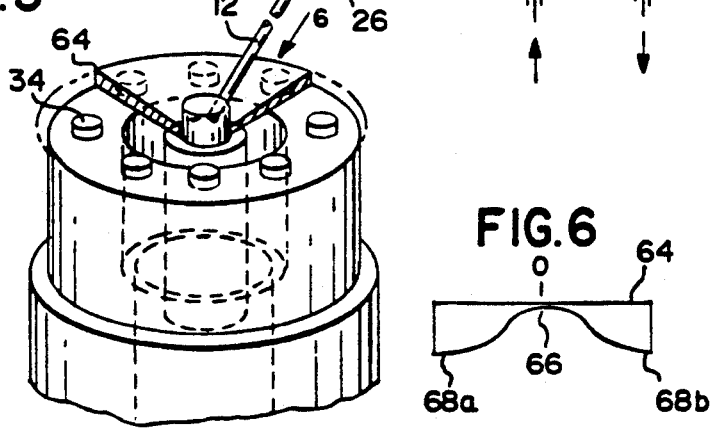

HYDRAULICALLY FLEXING CATHETER

BACKGROUND OF THE INVENTION

1. Field of the Invention

This invention relates to a catheter that has an expandable end portion containing longitudinally extending expandable channels which can be selectively pressurized so that the catheter expands radially adjacent the pressurized channel or channels and enables the catheter to be guided through bodily passageways. A mechanical rotary device can be manually adjusted to select the pressurized channels and enable the catheter to be directed as necessary.

2. Description of the Prior Art

Catheters, flexible endoscopes utilizing fiber optics quite often referred to as fiberscopes, and bronchoscopes are used widely in the medical field. Catheters are generally elongated tubes inserted into a body cavity or passageway to inject or withdraw fluids or other material. A flexible fiberoptic endoscope is used to perform internal observations in a body passage such as in a colonoscopy, and is valuable as an aid in performing procedures such as gall bladder removal without cutting the patient. Bronchoscopes are used for inspection of the trechea and bronchi. Catheters and such similar devices are used in diagnosing and treating many ailments and in virtually all passageways of the body, from blood vessels and urinary tracts to nasal and throat openings. They function to augment the flow of blood, air, urine, or as a means of treatment through drug delivery and removal of plaque and clots.

Navigating such devices through tortuous and/or branching bodily passageways is quite difficult. The services of skilled medical professionals is required if perforation of a passageway or other damage is to be avoided. Because of anatomical variations and pathological alterations even skilled, experienced professionals have great difficulty at times.

This invention is concerned with a unique catheter type of device that can be guided through the bodily passageways by providing a plurality of minute longitudinal channels adjacent the outside wall of an expandable front portion of the device, and manually operable means permitting the channels to be pressurized resulting in a turning of the front end of the device in the desired direction as it is passed through the desired bodily cavity.

Directional control of catheters is known in the art and described in U.S. Pat. No. 4,403,985 to Boretos. This device uses a pressurized control fluid which is expelled through control ports near the front end of the catheter. The pressurized fluid which escapes into the bodily cavity may be detrimental in some applications, and the present invention is preferable in all applications since no fluid is forced into the cavity. The device of Boretos is also expensive and complex. Other catheters using a plurality of projecting hollow nibs for assisting movement of a catheter through the bodily passage are shown in U.S. Pat. No. 3,665,928 to DelGuercio, and in U.S. Pat. No. 4,207,872 to Meiri et al, but neither of these devices is similar to the present invention.

SUMMARY OF THE INVENTION

In accordance with a preferred embodiment of this invention there is provided a catheter or similar device which is flexible at its forward end and which may be steered in a desired direction. A plurality of channels extend longitudinally along the outside of the catheter, and are equally spaced about its circumference. A piston assembly contains a plurality of pistons, one of which is connected through a conduit to each channel. Each conduit with its connecting channel is filled with a fluid which may be compressed selectively by manually actuating a piston connected with each channel. Upon compression of a piston, one channel, or more than one channel on one side of the device, expands adjacent the pressurized channel or channels, permitting the catheter end to move in the desired direction.

It is an object of this invention to provide a unique and novel apparatus for a catheter or the like which permits it to be guided in a desired direction within a bodily passageway.

Another object of this invention is a unique control device for pressurizing a radially expandable portion of a catheter or the like to permit it to be guided within a bodily passageway.

A still further object of this invention is a novel catheter or the like having a plurality of longitudinally extending channels within its forward end with means for pressuring selected ones of said channels for guiding said device through a bodily passageway.

BRIEF DESCRIPTION OF THE DRAWING FIGURES

The figures in the drawings are briefly described as follows:

FIG. 1 is a diagrammatic perspective view of the present invention;

FIG. 1A is a diagrammatic side view of the expandable channel portion;

FIG. 1B is a diagrammatic top view of the expandable channel portion with one channel pressurized and expanded;

FIG. 2 is an enlarged view of the invention with parts broken away;

FIG. 3 is a view with parts broken away in the direction of arrows 3—3 of FIG. 2;

FIG. 4 is an enlarged diagrammatic perspective view with parts broken away illustrating in detail the components of one embodiment of the invention;

FIG. 5 is an enlarged diagrammatic perspective view with parts broken away illustrating in detail the internal components of a second embodiment of the invention;

FIG. 6 is a diagrammatic view taken in the direction of arrow 6 along the circular edge of FIG. 5;

FIG. 7 is an enlarged diagrammatic cross-sectional view illustrating in greater detail the internal components of the invention; and FIG. 8 illustrates the relative reciprocating nature of the components of the invention.

DESCRIPTION OF THE PREFERRED EMBODIMENT

Referring to FIG. 1 there is shown a circular piston assembly 10, shown more particularly in FIG. 4, which includes a steering arm 12 extending radially from the top thereof. The piston assembly 10 narrows at its base into a conduit assembly 14 which is adapted at its lowermost extension to mate with a female socket assembly 16 forming the rearmost end of a catheter 18. Catheter 18 may be a catheter, endoscope, bronchoscope, or other similar type of apparatus which is used within bodily cavities. A plurality of channels 20 extend longitudinally along the catheter 18 as best shown in FIGS.

1A and 1B which are enlarged views of the catheter 18. In FIG. 1B one of the channels 20a has been pressurized and the outside of the catheter 18 adjacent thereto has expanded as will be described. The channels 20 are preferably evenly spaced about the circumference of the catheter 18.

The forward end of the Catheter 18 comprises an expandable channel region 22 which is preferably composed of plastic such as an elastomeric material. The catheter 18 may be a hollow center so as to have a conduit formed therein, or a solid center such as a fiberscope. The expandable region 22 is adapted to expand adjacent any channel 20 which is pressurized (FIG. 1B) in order to steer the catheter through the body cavity into which it is inserted.

In FIG. 2 at socket assembly 16 there is shown at 24 the ends of channels 20. Eight such channels 20 are shown in illustration thereof. Coextensive with channels 20 and ends 24 are an identical number of conduits 26 within the piston assembly 10 and extending through the conduit assembly 14. As best seen in FIGS. 2 and 3, the lowermost ends of conduits 26 extend slightly beyond the end of conduit assembly 14 and a mate snugly within ends 24 of socket assembly 16 so that channels 20 are continuations of conduits 26.

As shown best in FIG. 4, conduits 26 extend into the circular piston assembly 10 leading to the bottom of a plurality of cylinders 28 formed within wall 30 of piston assembly 10. Each cylinder 28 contains a piston head 32 connected to a piston shaft 34. In FIG. 7 the piston is shown in its normal position where shaft 34 extends a slight distance beyond the top of wall 30. Spring 36 is seated on a ledge 38 formed by the outside wall of channel 26 to push against the bottom of piston head 32 and maintain the piston as shown in FIG. 7. As will be described, piston shaft 34 can be forced downwardly (arrow 40) in which case spring 36 will compress and act to force the piston back to its normal position when the downwardly acting force is removed.

As best shown in FIG. 4 a fluid 42 such as a saline solution or one having a pH to match the bodily cavity into which it will be inserted is maintained in each cylinder 28 and in conduits 26 as well as channels 20 in catheter 18. Piston rings 43 prevent the fluid 42 from leaking past the piston head 32. When the piston shaft 34 is forced downwardly, the fluid 42 is compressed causing the channel 20 in the expandable region 22 in which the fluid is pressurized to expand slightly. When a channel 20 is pressurized, the outside of the catheter 18 adjacent the pressurized channel is enlarged (see FIG. 1B), and the end 22 of the catheter 18 will meet restraints if it attempts to move in the direction of the expanded portion of the catheter 18. Thus by controlling the movement of the pistons, and thereby the expansion of the channels 20 connected thereto, the catheter 18 may be directed through the body cavity as desired.

In FIG. 4 is also shown a turn housing holding therein a rotatable screw member 46 extending upward through sleeve 48. The screw member 46 is secured by a bolt 50. The sleeve 48 will rotate with the screw member 46 about the axis of the screw member 46. Extending from the sleeve 48 is an arm 52 on which is mounted a roller 54 of substantial mass. The roller is rotatable about arm 52 as shown by arrow 56.

Arm 52 and its extension 12 acts as a lever so that manual movement of arm 12 in a direction shown by arrow 58 will rotate sleeve 48 and screw member 46. As a consequence, roller 54 which is in contact with and moves over the top of wall 30 will push downwardly on a piston when the roller 54 comes in contact with the piston shaft 34 extending above the wall 30. The piston will push downwardly against its spring 36 in the cylinder 38 and cause an increase in the pressure of the fluid 42 in the conduit 26 and channel 20 in which the fluid is contained. The expandable end 22 of the catheter 18 containing the pressurized channel 20 will expand as illustrated in FIG. 1B. Thus by manually moving arm 12 it is possible to select any one piston to be moved downwardly and thus the channel 20 which will expand in region 22. This will effectively prevent the catheter from moving in the direction of the expanded channel, and will enable the catheter 18 to be guided as it moves within the selected bodily cavity.

The pressure of the fluid 42 within the channels 20 may be varied by turning turn housing 44 which in turn will raise or lower screw member 46 and sleeve 48. This will in turn raise or lower roller 54 relative to the top of wall 30 and the distance a piston is depressed when in contact with the roller 54.

FIG. 8 shows at 60 the piston in its normal position having its shaft 34 extending above the top of wall 30, and at 62 the piston in the position when it has been depressed by the roller 54.

Better control over the direction of movement of the catheter 18 is possible if more than one channel 20 is pressurized at the same time. This will produce expansion of region 22 of the catheter 18 over a larger circumferential area. As seen in FIG. 5, a sector shaped planar element 64 having a flat bottom is attached to arm 12 in place of the roller 54. As illustrated, the outside circumference of the element 64 is sufficient to depress three pistons simultaneously, although it is apparent that two or four pistons can be depressed by making element 64 to have smaller or larger circumferential area. Depression of two to four adjacent pistons simultaneously will cause expansion of the corresponding number of adjacent channels 20 in region 22, and provide improved control of the movement of the catheter 18 in many situations.

A still further enhancement of the invention may be had by designing planar element 64 as shown in the view of FIG. 6, which is a view looking at the element from the direction of arrow 6 in FIG. 5. If the center of the planar element 64 is cut away as shown at 66, only the end regions of the planar element 64 shown at 68a and 68b will come into contact with and depress the pistons over which the element 64 is positioned. Consequently, alternate channels 20 will be pressurized and expand in region 22. This geometry may be advantageous in certain applications.

While the invention has been described with respect to preferred embodiments thereof, it is apparent that the changes may be made to the construction and arrangement of the components and their use without departing from the scope of the invention as hereinafter claimed.

What is claimed is:

1. A catheter adapted to be directed through a tortuous or branching bodily passageway comprising:
 a) a narrow, circular catheter tube having a radially expandable region at its forward end and a larger diameter socket contiguous with said tube at its rearward end, said catheter tube and said socket having a plurality of longitudinally extending narrow channels embedded therein evenly spaced about the circumference of said tube and immediately adjacent the outer surface thereof, each said channel being filled with fluid with said expandable region being adapted to expand slightly and stiffen in the area surrounding each channel having the fluid therein under pressure; and b) manually operated means connected with said socket for selectively pressurizing the fluid in selected ones of said channels and comprising:

i) a piston assembly of circular cross-section and with a central axis, containing therein a plurality of cylinders evenly spaced about a circumference of said piston assembly each containing a piston, the number of cylinders being equal to the number of channels, each said piston comprising a circular head member having two flat sides, a shaft member extending from one side of said head member, and spring means within said cylinder and bearing against the other side of said head member for maintaining said piston in said cylinder so that a portion of said shaft member extends through said cylinder and a short distance above said circular assembly when said piston is not actuated, said piston assembly having a circular socket adapter at one end thereof configured to mate with said socket whereby each said piston is connected with on of said channels; and ii) actuator means connected with said circular piston assembly for selectively moving one or more of said pistons to pressurize the fluid within the channel to which said actuated pistons are connected said actuator means comprising:

a rotatable shaft member parallel with said piston shaft member and adapted to rotate about the central axis of said circular assembly;

an arm attached to and extending radially from said rotatable shaft member in a plane substantially parallel with a topmost extension of said piston shaft members, said arm being adapted to be moved manually about said rotatable shaft; and mechanical means attached to said arm and movable therewith form contacting and depressing at least one of said extending piston shaft member upon movement of said arm.

2. A catheter as in claim 1 in which said mechanical means comprises a roller mounted on said arm and rotatable upon movement of said arm, said roller being adapted to depress only one of said piston shaft members.

3. A catheter as in claim 1 in which said mechanical means comprises a sector shaped planar element mounted on said arm and adapted to depress more than one of said piston shaft members.

4. A catheter as in claim 3 in which said sector shaped planar element has a depressed portion in the center thereof whereby said element will depress alternate ones of said piston shaft members.

5. A catheter as in claim 1 in which the expandable portion of said catheter is composed of an elastomeric material.

6. A catheter as in claim 1 in which said piston assembly of circular cross-section includes circular members extending from each channel so as to mate within the channels within said socket.

7. A catheter adapted to be directed through a tortuous or branching bodily passageway comprising:

a) a narrow, circular catheter tube having a radially expandable region at its forward end and a larger diameter socket contiguous with said tube at its rearward end, said catheter tube and said socket having a plurality of longitudinally extending narrow channels embedded therein evenly spaced about the circumference of said tube and immediately adjacent the outer surface thereof, each said channel being filled with fluid with said expandable region being adapted to expand slightly and stiffen in the area surrounding each channel having the fluid therein under pressure; and b) manually operated means connected with said socket for selectively pressurizing the fluid in selected ones of said channels and comprising:

i) a piston assembly of circular cross-section containing therein a plurality of cylinders arranged about a circumference of said piston assembly each cylinder containing a piston, the number of cylinders being equal to the number of channels, said piston assembly having a circular socket adapter at one end thereof configured to mate with said socket whereby each said piston is connected with one of said channels; and ii) actuator means connected with said circular piston assembly for rotation about a central axis thereof along the circumference into selective engagement with one or more of said pistons thereby selectively moving one or more of said pistons to pressurize the fluid within the channel to which said actuated pistons are connected.

* * * * *